United States Patent [19]

Coles et al.

[11] 3,976,784
[45] Aug. 24, 1976

[54] METHOD OF TREATMENT OF LIVER FLUKE INFECTIONS

[75] Inventors: Gerald Christopher Coles; Justus Kenneth Landquist, both of Macclesfield, England

[73] Assignee: Imperial Chemical Industries Limited, London, England

[22] Filed: Jan. 16, 1975

[21] Appl. No.: 541,694

[30] Foreign Application Priority Data
Feb. 4, 1974 United Kingdom............... 5014/74

[52] U.S. Cl............................... 424/324; 424/233; 424/347; 424/350
[51] Int. Cl.$^2$....................................... A61K 31/165
[58] Field of Search........................... 424/233, 324

[56] References Cited
UNITED STATES PATENTS

| | | | |
|---|---|---|---|
| 3,466,370 | 9/1969 | Broome et al. | 424/233 |
| 3,708,517 | 1/1973 | Ugi | 260/465 D |
| 3,798,258 | 3/1974 | Patchett et al. | 424/324 |

OTHER PUBLICATIONS

Chemical Abstracts, vol. 54 (1960), p. 19593h.

*Primary Examiner*—V. D. Turner
*Attorney, Agent, or Firm*—Cushman, Darby & Cushman

[57] ABSTRACT

A method for treating domestic animals infected with liver fluke which comprises administering, alone or in combination with known agents, a mono- or di-acyl derivative of 4,4'-diaminodiphenyl sulphide. Also disclosed are veterinary compositions containing such an active ingredient. The preferred ingredient is 4,4'-diacetamidodiphenyl sulphide.

3 Claims, No Drawings

METHOD OF TREATMENT OF LIVER FLUKE INFECTIONS

This invention relates to a method of treatment of a domestic animal infected with liver fluke.

According to the invention there is provided a method for the treatment of a domestic animal infected with liver fluke which comprises administering to said animal an effective amount of a compound of the formula:

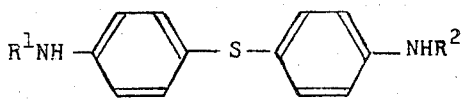

(Formula I)

wherein $R^1$ is an alkanoyl radical of up to 6 carbon atoms and $R^2$ is hydrogen or an alkanoyl radical of up to 6 carbon atoms.

A suitable value for $R^1$, or for $R^2$ when it stands for an alkanoyl radical, is, for example, the formyl or acetyl radical.

Preferably both $R^1$ and $R^2$ are alkanoyl radicals, and $R^1$ and $R^2$ are more preferably both acetyl radicals.

According to a further feature of the invention there is provided a veterinary composition which comprises a compound of Formula I given above, wherein $R^1$ and $R^2$ have the meanings stated above, together with a veterinarily-acceptable diluent or carrier therefor.

The compound of Formula I, or the composition of the invention, is conveniently administered to a domestic animal either orally or parenterally, by conventional means. Suitable oral compositions are, for example, aqueous suspensions, dispersions or drenches, boluses, tablets, capsules, oily solutions or suspensions, oil-in-water emulsions, dispersible powders, premixes suitable for addition to animal foodstuffs, or mixtures with animal foodstuffs. Suitable parenteral compositions are sterile aqueous or oily suspensions or oily solutions which have been sterilised by conventional techniques.

The compositions of the invention may contain standard excipients known to the art to be useful in the formulation of such compositions and they may contain where appropriate, for example, inert diluents, fillers, disintegrating agents, bacteriostats, bactericidal agents, sporicidal agents, stabilising agents, thickening agents, preservatives, wetting agents, binding agents, lubricating agents, dispersing or emulsifying agents, suspending agents, sweetening agents, flavouring agents and pharmaceutically-acceptable colouring agents. The compositions may also optionally contain other substances of veterinary utility such as vitamins and mineral salts.

The aqueous suspensions, dispersions or drenches of the invention may contain one or more suitable suspending or thickening agents, for example sodium carboxymethylcellulose; wetting agents, for example condensation products of fatty alcohols with ehtylene oxide; or preservatives, for example methyl or propyl p-hydroxybenzoate. They may also contain one or more sweetening agents, for example glycerol, dextrose or sucrose, or flavouring agents, for example vanillin or orange extract, in order to provide a palatable product.

Suitable tablets and boluses may be formulated by admixture of the active ingredient with one or more known pharmaceutical excipients, for example inert diluents, for example calcium carbonate, calcium phosphate or lactose; disintegrating agents, for example maize starch or alginic acid; binding agents, for example starch, gelatin or acacia mucilage; lubricating agents, for example magnesium stearate, stearic acid or talc; or wetting agents, for example alkali metal salts of sulphonated dialkylnaphthalenes. Such tablets may optionally be coated by known techniques in order to delay disintegration in the upper gastro-intestinal tract.

Compositions in the form of capsules may consist, for example, of gelatine capsules containing active ingredient only, or the active ingredient in admixture with one or more inert diluents, for example lactose or sorbitol, or the active ingredient in solution or suspension in a vegetable oil.

The oily solutions of the invention may contain the active ingredient in solution in a suitable fat of vegetable or animal origin, for example arachis oil or cod-liver oil, and may optionally contain one or more sweetening or flavouring agents to mask the taste and improve oral acceptability. The oily suspensions may be oily solutions which also contain a sweetening agent, such as icing sugar, in which case the oil phase may in addition contain a suspending agent, for example beeswax, to maintain the redispersion properties of the suspension.

The oil-in-water emulsion compositions of the invention may similarly contain the active ingredient dissolved in a suitable fat of vegetable or animal origin, and may also contain one or more sweetening or flavouring agents. The emulsions may also contain one or more emulsifying or dispersing agents, for example soya bean lecithin, polyoxyethylene sorbitan monooleate, gum acacia, gum tragacanth or casein, and one or more preservatives, for example methyl or propyl p-hydroxybenzoate, or anti-oxidants, for example propyl gallate.

The dispersible powders of the invention may contain the active ingredient in admixture with suitable wetting, dispersing and suspending agents.

The premixes of the invention preferably contain between 1% and 25% be weight of the active ingredient and may contain the active ingredient in admixture with one or more non-toxic diluents or carriers, for example talc, kaolin, chalk, lactose, urea, corn or meal, ground oyster shells, distillers' dried grains or edible vegetable substances, for example commercial animal foodstuffs.

The mixtures with animal foodstuffs which are intended to be orally administered as such to domestic animals preferably contain between 0.01% and 2% by weight of the active ingredient.

The sterile injectable aqueous suspensions of the invention may contain a suspending or thickening agent, for example sodium carboxymethylcellulose, and a wetting or dispersing agent, for example a phenolpolyethylene oxide condensate, for example the condesation product of octylcresol with about 8–10 molecular proportions of ethylene oxide. The injectable oily solutions of the invention may be prepared from a non-toxic injectable fat or oil, for example arachis oil or ethyl oleate, and they may additionally contain gelling agents, for example aluminium stearate, to delay absorption within the body. These aqueous and oily injectable preparations may contain preservatives such as methyl or n-propyl p-hydroxybenzoate or chlorobutanol.

The compound of Formula I wherein $R^1$ and $R^2$ both stand for the same alkanoyl radical may be obtained by acylation of the known compound 4,4′-diaminodiphenyl sulphide with an acylating agent derived from an acid of the formula $R^1OH$.

The compound of Formula I wherein $R^2$ stands for hydrogen may be obtained by reduction of a compound of the formula:

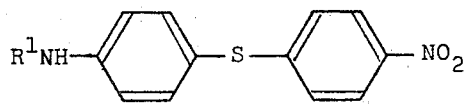

(Formula II)

wherein $R^1$ has the meaning stated above, which compound itself may be obtained by acylation of the known compound 4-amino-4′-nitrodiphenyl sulphide with an acylating agent derived from an acid of the formula $R^1OH$.

The compound of Formula I wherein $R^2$ stands for an alkanoyl radical different from $R^1$ may be obtained by acylation of the corresponding compound wherein $R^2$ stands for hydrogen with an acylating agent derived from an acid of the formula $R^2 OH$.

The compound of Formula I is particularly effective in eradicating immature liver fluke, that is fluke less than 10 to 12 weeks old, from domestic animals, whereas most commercially-available fasciolicides are more effective against mature liver fluke, that is, fluke more than 10 to 12 weeks old, and indeed many such available compounds are barely effective against immature fluke. Accordingly, use of the compound of Formula I provides a valuable complementary treatment when used in conjunction with existing remedies.

According to a further feature of the invention there is provided a method for the treatment of a domestic animal infected with liver fluke which comprises administering concomitantly to said animal an effective amount of a compound of Formula I given above, wherein $R^1$ and $R^2$ have the meanings stated above, and an effective amount of at least one agent known to be useful for the treatment of domestic animals infested with mature liver fluke.

By use of the expression "administering concomitantly" it is to be understood that the two (or more) active agents are either administered simultaneously, by the same or different routes, or they are administered at an appropriate time interval so that the maximum advantage is derived from the combined therapy. Such a time interval is readily ascertainable by an expert in the field. Thus, for example, if the agents are to be administered simultaneously, this can be done by administering a combination formulation as hereinafter defined as a further feature of this invention, or by simultaneously administering separate formulations of the two or more active agents by the same or different routes. Alternatively, if there is to be a time interval between the administration of the two or more agents, said agents can be administered in suitable formulations at appropriate times. Preferably both active agents are administered orally.

According to a further feature of the invention there is provided a veterinary composition which comprises in combination i. a compound of Formula I given above, wherein $R^1$ and $R^2$ have the meanings stated above; and ii. an agent known to be useful for the treatment of domestic animals infected with mature liver fluke; and, optionally, iii. a veterinarily-acceptable diluent or carrier therefor.

The combination composition of the invention may be of a type described above for a veterinary composition containing a compound of Formula I as active ingredient, and is preferably in a form suitable for oral administration.

A suitable agent known to be useful for the treatment of domestic animals infected with mature liver fluke is, for example, a chlorinated hydrocarbon, for example carbon tetrachloride, ethane hexachloride, hexachlorophane or 1,4-bistrichloromethylbenzene, or a nitrophenol derivative, for example niclofolan or nitroxynil, or a halogenated salicylanilide derivative, for example oxyclozanide or a related penta- or hexa-halogeno derivative disclosed in U.K. Specification No. 1,048,084 or 1,050,767, or rafoxanide, clioxanide, dibromsalan or tribromsalan, or a compound disclosed in German Specification No. 2,259,527.

A preferred agent known to be useful for the treatment of domestic animals infected with mature liver fluke is a salicylanilide derivative of the formula:

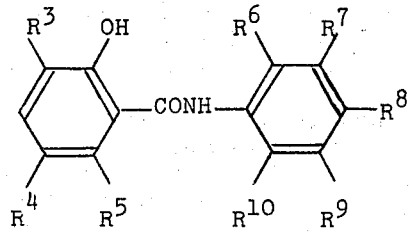

(Formula III)

wherein either:

a. $R^3$ and $R^4$ are both chlorine or both bromine and $R^5$ is hydrogen, or $R^3$, $R^4$ and $R^5$ are all chlorine; $R^6$ is hydroxy; and $R^7$ and $R^9$ are both chlorine and $R^8$ and $R^{10}$ are both hydrogen, or $R^7$, $R^9$ and $R^{10}$ are all chlorine and $R^8$ is hydrogen, or $R^7$, $R^8$, $R^9$ and $R^{10}$ are all chlorine; or $R^3$ and $R^4$ are both bromine or both iodine and $R^5$ is hydrogen; and either $R^6$ and $R^8$, or $R^7$ and $R^8$, or $R^8$ and $R^9$ are both chlorine or both bromine and $R^{10}$ and the other two of $R^6$, $R^7$, $R^8$ and $R^9$ are all hydrogen.

The particular preferred agent as defined under (a) above is the compound of Formula III wherein $R^3$, $R^4$, $R^5$, $R^7$ and $R^9$ are all chlorine, $R^6$ is hydroxy and $R^8$ and $R^{10}$ are both hydrogen, which compound is oxyclozanide.

The particularly preferred agent as defined under (b) above is the compound of Formula III wherein $R^3$ and $R^4$ are both iodine, $R^5$, $R^6$, $R^8$ and $R^{10}$ are all hydrogen and $R^7$ and $R^9$ are both chlorine. This compound, hereinafter described as "ICIA 8203", is disclosed in German Specification No. 2,259,527.

A preferred combination composition of the invention will contain between 4 and 5 parts by weight of the preferred compound of Formula I (wherein $R^1$ and $R^2$ are both acetyl) together with one part by weight of oxychlozanide, or between 15 and 30 parts by weight of the preferred compound of Formula I together with one part by weight of ICIA 8203.

A veterinary composition of the invention may also optionally contain, in addition to a compound of Formula I or such a compound together with an agent known to be useful for the treatment of domestic animals infected with mature liver fluke, one or more further drugs of known veterinary utility, for example anthelmintic agents, for example tetramisole, levamisole, methyridine or thiabendazole, and growth promoting agents, for example antibacterial substances or anabolic steroids.

The invention is illustrated but not limited by the following Examples.

EXAMPLE 1

Four groups each of 5 Welsh ewes, the individual animal weights being in the range 23–40 kg., were treated as follows:

Group 1: each ewe was infected with 1,000 metacercariae of *Fasciola hepatica* and then given an oral dose of 65 mg. per kg. bodyweight of 4,4'-diacetamidodiphenyl sulphide 3 weeks after infection.

Group 2: each ewe was infected as in Group 1, but the 65 mg. per kg. dose of 4,4'-diacetamidodiphenyl sulphide was given 6 weeks after infection.

Group 3: each ewe was infected as in Group 1 but no dose of compound was given.

Group 4: no ewe was deliberately infected, but each ewe was given an oral dose of 325 mg. per kg. bodyweight of 4,4'-diacetamidodiphenyl sulphide.

The animals in Groups 1, 2 and 3 were all killed 7 weeks after infection and their livers examined. Ewes in Group 3 had a mean infestation of 278 fluke in the liver. Ewes in Group 1 had a mean infestation of 2 fluke in the liver, that is, when compared with Group 3 animals 99% of the fluke had been eliminated. Ewes in Group 2 had a mean infestation of 47 fluke in the liver, that is, when compared with Group 3 animals 83% of the fluke had been eliminated.

No symptoms of toxicity were seen in any animal in Group 4.

EXAMPLE 2

Sorbitan monostearate ('Span'-60; 0.1 g.) and polyoxyethylene sorbitan monooleate ('Tween'-80; 0.1 g.) are added to a heated (75°–80°C.) solution of methyl p-hydroxybenzoate (0.03 g.) and propyl p-hydroxybenzoate (0.003 g.) in water (11 ml.) and the solution is cooled to 30°C. 4,4'-Diacetamidodiphenyl sulphide (8 g.) is then dispersed in this solution. The dispersion is added to a heated (75°–80°C.) mixture of 'Veegum' HV (0.8 g.), methyl p-hydroxybenzoate (0.12 g.), propyl p-hydroxybenzoate (0.012 g.), sodium citrate (0.5 g.) and sodium carboxymethylcellulose ('Edifas' - B.50; 0.9 g.) in water (72 ml.), sodium metabisulphite (0.1 g.) is added and water is added to make the volume of the mixture up to 100 ml. The mixture is homogenised, and there is thus obtained a drench suitable for oral administration to domestic animals ('Span', 'Tween', 'Veegum' and 'Edifas' are Trade Marks).

EXAMPLE 3

The process described in Example 2 is repeated except that 6.5 g. of 4,4'-diacetamidodiphenyl sulphide and 1.5 g. of oxyclozanide are used in place of the 8 g. of 4,4'-diacetamidodiphenyl sulphide. There is thus similarly obtained a drench suitable for oral administration to domestic animals.

EXAMPLE 4

The process described in Example 2 is repeated except that 7.5 g. of 4,4'-diacetamidodiphenyl sulphide and 0.5 g. of 3', 5'-dichloro-3,5-diiodosalicylanilide (ICIA.8203) are used in place of the 8 g. of 4,4'-diacetamidodiphenyl sulphide. There is thus similarly obtained a drench suitable for oral administration to domestic animals.

EXAMPLE 5

The process described in Example 2, 3 or 4 is repeated except that 4-acetamido-4'-aminodiphenyl sulphide is used in place of 4,4'-diacetamidodiphenyl sulphide. There is thus similarly obtained a drench suitable for oral administration to domestic animals.

EXAMPLE 6

The process described in Example 2, 3 or 4 is repeated except that 4,4'-diformamidodiphenyl sulphide is used in place of 4,4'-diacetamidodiphenyl sulphide. There is thus similarly obtained a drench suitable for oral administration to domestic animals.

What we claim is:

1. A method for the treatment of a sheep infected with immature liver flukes which comprises orally administering to said sheep an amount effective for eradicating said immature liver flukes of a compound of the formula:

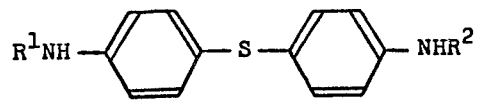

[Formula I]

wherein $R^1$ is alkanoyl of 1 to 6 carbon atoms and $R^2$ is hydrogen or alkanoyl of 1 to 6 carbon atoms.

2. A method as claimed in claim 1 wherein $R^1$ is formyl or acetyl, and wherein $R^2$ is hydrogen, formyl or acetyl.

3. A method as claimed in claim 1 wherein $R^1$ and $R^2$ are both acetyl.

* * * * *